United States Patent [19]

Siegel et al.

[11] Patent Number: 5,395,975
[45] Date of Patent: Mar. 7, 1995

[54] PREPARATION OF POLYACYLATED AROMATIC COMPOUNDS

[75] Inventors: Wolfgang Siegel, Mannheim; Jochen Schroeder, Limburgerhof, both of Germany

[73] Assignee: BASF Aktiengesellschaft, Ludwigshafen, Germany

[21] Appl. No.: 158,788

[22] Filed: Dec. 1, 1993

[30] Foreign Application Priority Data

Dec. 5, 1992 [DE] Germany .................... 42 40 966.7

[51] Int. Cl.⁶ ................................................ C07C 45/45
[52] U.S. Cl. ..................................... 568/316; 568/323
[58] Field of Search ................................ 568/323, 316

[56] References Cited

U.S. PATENT DOCUMENTS

| | | | |
|---|---|---|---|
| 2,322,036 | 6/1943 | Lieber et al. | 568/323 |
| 2,346,926 | 4/1943 | Lieber et al. | 568/323 |
| 2,802,032 | 8/1957 | Prill | 568/323 |
| 4,922,026 | 5/1990 | Baker, Jr. et al. | 568/322 |

FOREIGN PATENT DOCUMENTS

| | | | |
|---|---|---|---|
| 515 540 | 1/1931 | Germany | 568/323 |
| 2235195 | 2/1991 | United Kingdom | 568/323 |
| 368223 | 4/1973 | U.S.S.R. | 568/323 |
| 1016277 | 5/1983 | U.S.S.R. | 568/323 |

OTHER PUBLICATIONS

Chem. Abst. vol. 86, No. 25, Jun. 20, 1977, Abst. No. 189401w.
Zh. Org. Khim. 6 (1970) 532.
Org. Prep. Proc. Int. 10 (1978) 255.
Zh. Org. Khim. 6 (1970) 535.
Synthesis (1972) 533.
Jensen et al., "Friedel-Crafts & Related Reactions", Tutuscience Publishers, vol. 3, part 2, pp. 1020–1022 (1964).

*Primary Examiner*—James H. Reamer
*Attorney, Agent, or Firm*—Keil & Weinkauf

[57] ABSTRACT

Polyacylated aromatic compounds of formula I

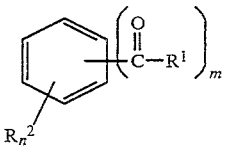

where
R¹ is phenyl which is unsubstituted or has inert substituents or is α-halo-$C_1$–$C_6$-alkyl, it being possible for these radicals to be identical or different;
R² is $C_1$–$C_4$-alkyl;
m is 2 or 3;
n is 0 to 4, it being possible for the R² substituents to be different when n>1, with the proviso that m+n≦6, are prepared by reacting an acylaromatic compound of the formula II

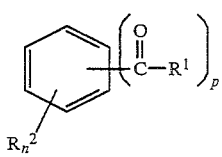

where p is 1 or 2, with a carbonyl halide of the formula III

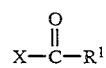

where X is halogen, in an amount appropriate for the desired degree of acylation, in the presence of Fe(II), Fe(III), Zn(II), Mo(VI), W(VI) or Sn(IV) compounds.

5 Claims, No Drawings

PREPARATION OF POLYACYLATED AROMATRIC COMPOUNDS

The present invention relates to a novel process for preparing polyacylated aromatic compounds of the formula I

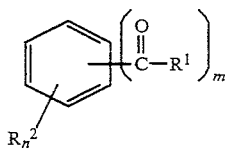

where
- $R^1$ is phenyl which is unsubstituted or has inert substituents or is $\alpha$-halo-$C_1$-$C_6$-alkyl, it being possible for these radicals to be identical or different;
- $R^2$ is $C_1$-$C_4$-alkyl;
- m is 2 or 3;
- n is 0 to 4, it being possible for the $R^2$ substituents to be different when n>1, with the proviso that m+n≦6.

The introduction of a second acyl group into acylaromatic compounds is difficult because acyl groups inactivate aromatic compounds for further Friedel-Crafts acylations.

Zh. Org. Khim. 6 (1970) 532 describes how another benzoyl group can be introduced into highly activated 2,4-dimethoxybenzophenone by reaction with benzoyl chloride in the presence of catalytic amounts of finely divided iron powder or FeCl₃.

Org. Prep. Proc. Int. 10 (1978) 255 discloses direct Friedel-Crafts diacylation of trimethyl- and tetramethylbenzenes in the presence of AlCl₃. Large molar excesses of carbonyl chloride and AlCl₃ are necessary for this; not only are these uneconomic, the conventional hydrolytic workup often leads to waste water containing hydrochloric acid, which requires elaborate disposal.

Direct reaction of anisole, which is highly activated, with benzoyl chloride in the presence of iron powder to give 2,4-dibenzoylanisole is described in Zh. Org. Khim. 6 (1970) 535.

Monoacylation of aromatic compounds with catalytic amounts of FeCl₃, iodine, ZnCl₂ and iron powder is disclosed in Synthesis (1972) 533.

It is an object of the present invention to provide a process for introducing further acyl groups into unsubstituted or $C_1$-$C_4$-alkyl-substituted acylaromatic compounds without equimolar amounts of Friedel-Crafts catalysts being required. It is also an object of the present invention to find a process for the direct preparation of polyacylated aromatic compounds from aromatic compounds with only catalytic amounts of catalysts in only one step.

We have found that this object is achieved by the process defined above, which comprises reacting an acylaromatic compound of the formula II

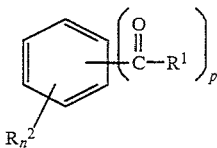

where p is 1 or 2, with a carbonyl halide of the formula III

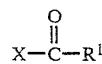

where X is halogen, in an amount appropriate for the desired degree of acylation, in the presence of Fe(II), Fe(III), Zn(II), Mo(VI), W(VI) or Sn(IV) compounds.

The process can be represented by the following equation:

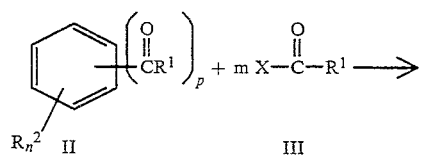

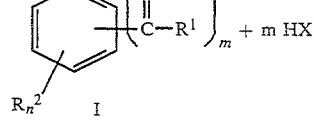

The starting compounds II are known or can be obtained by known methods. The $R^2$ substituents are $C_1$-$C_4$-alkyl, e.g. ethyl, n-propyl and n-butyl, but preferably methyl.

In a particularly preferred embodiment, the compounds II are prepared in situ from automatic compounds IV

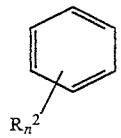

such as benzene, toluene, o-xylene, m-xylene, p-xylene and, in particular, tri- and tetra-$C_1$-$C_4$-alkyl-substituted benzenes such as 1,3,5-trimethylbenzene (mesitylene), 1,3,5-triethylbenzene, 1,2,4,5-tetramethylbenzene (durene) and 1,2,3,5-tetramethylbenzene (isodurene).

The compounds II or IV are reacted with carbonyl halides III, with the chlorides being preferred. Suitable benzoyl halides are those in which the phenyl radical carries substituents which are inert under the reaction conditions, such as nitro, halogen such as fluorine, chlorine and bromine, $C_1$-$C_6$-alkoxy such as methoxy and $C_1$-$C_4$-alkyl such as methyl. It is also possible to use aliphatic α-halo-$C_1$-$C_6$-carboxylic acids such as 2-haloacetic and 2-halopropionic acids in the process according to the invention. Preferred examples are benzoyl chloride, 4-fluorobenzoyl chloride, 4-chlorobenzoyl chloride, 4-nitrobenzoyl chloride, 2-methylbenzoyl chloride and chloroacetyl chloride.

The reaction is catalyzed by a number of metal compounds complying with the definition. Suitable compounds are those of Fe(II) such as $FeSO_4$, Fe(III) such as $Fe_2O_3$, $FeCl_3$, $FeBr_3$, $Fe_2(SO_4)_3$, iron carboxylates such as iron(III) acetate, iron(III) acetylacetonate, and, of course, mixed valency iron compounds such as $Fe_3O_4$, as well as zinc(II) compounds such as ZnO, $ZnCl_2$, $ZnBr_2$, $ZnSO_4$, zinc carboxylates such as zinc benzoate and zinc acetate, molybdenum and tungsten(VI) compounds such as $MoO_3$ and $WO_3$, as well as tin(IV) compounds such as tin tetrachloride or tin tetrabromide. The iron compounds are the preferred catalysts, and iron oxide $Fe_2O_3$ is particularly preferred. The said compounds can be used in free form or else bound to inert carriers, suitable examples being silica, alumina or alumosilicates.

The molar ratios of the compounds II and III can vary depending on the required degree of acylation. However, the ratio is usually from 1:1 to 1.3:1 equivalents of carbonyl halides to aromatic compound II which already has acyl groups for monoacylation. An excess is generally employed for diacylations so that the molar ratios for III:II in this case are from 3:1 to 10:1. If the aromatic compound IV is used as starting material, at least one equivalent more of carbonyl halide must be used.

The catalyst can be used in amounts of from 0.01 to 20 mol %, preferably from 0.1 to 3 mol %, based on the amount of acylaromatic compound II or aromatic compound IV.

The reaction is usually carried out at from 40° to 250° C., preferably from 80° to 200° C., and particularly preferably from 100° to 180° C.

The pressure plays no evident part in the process according to the invention. The reaction can therefore be carried out under from 1 to 10 bar, but atmospheric pressure is preferred. The reaction can be carried out by mixing the starting compounds and the catalyst and heating to the appropriate temperature. However, it is preferred to mix the starting material II or IV and the catalyst and to add, at elevated temperature, the carbonyl halide III.

The reaction can, in the preferred embodiment, take place without solvent, but inert solvents such as nitrobenzene or hydrocarbons can also be used.

The reaction is generally complete after from 2 to 6 hours. The products are isolated by conventional methods such as distillation or crystallization.

The process according to the invention allows polyacylated aromatic compounds to be prepared from an acylaromatic compound and carbonyl halides in good yields. Only catalytic amounts of a metal compound are used for this. The reaction can be carried out without solvent and does not require hydrolytic workup. Furthermore, the invention allows polyacylated aromatic compounds to be prepared from benzene or $C_1$–$C_4$-alkyl-substituted benzenes.

The products prepared by the process are used as monomers for polyaryl ethers (GB 2 235 195).

EXAMPLES

General Method for the Examples 1 mol of a substituted benzene IV and catalyst were heated to temperature $T_1$, the carbonyl chloride III was added, and the mixture was heated at temperature $T_2$ for time t. The product was isolated by distillation or crystallization from heptane.

Further details are to be found in the Table.

TABLE

| Example | Benzene IV | Carbonyl chloride III | Amount of catalyst | $T_1$ [°C.] | $T_2$ [°C.] | t [h] | Product I | Yield [%] |
| --- | --- | --- | --- | --- | --- | --- | --- | --- |
| 1 | 1,3,5-trimethyl- | 4-chlorobenzoyl 2.2 mol | $Fe_2O_3$ 10 mmol | 100 | 150 | 4 | 1,3-bis(4-chlorobenzoyl)-2,4,6-trimethylbenzene | 80 |
| 2 | 1,3,5-trimethyl- | benzoyl 2.2 mol | $Fe_2O_3$ 10 mmol | 100 | 150 | 4 | 1,3-bisbenzoyl-2,4,6-trimethylbenzene | 79 |
| 3 | 1,3,5-trimethyl- | benzoyl 6.0 mol | $Fe_2O_3$ 25 mmol | 100 | 180 | 3 | 1,3,5-trisbenzoyl-2,4,6-trimethylbenzene | 73 |
| 4 | 1,3,5-trimethyl- | 4-nitrobenzoyl 2.2 mol | $Fe_2O_3$ 10 mmol | 120 | 160 | 2 | 1,3-bis(4-nitrobenzoyl)-2,4,6-trimethylbenzene | 90 |
| 5 | 1,3,5-trimethyl- | 2-methylbenzoyl 2.1 mol | $Fe_2O_3$ 15 mmol | 100 | 150 | 2 | 1,3-bis(2-methylbenzoyl)-2,4,6-trimethylbenzene | 80 |
| 6 | 1,3-dimethyl- | benzoyl 2.0 mol | $Fe_2O_3$ 25 mmol | 140 | 170 | 2 | Mixture of 1,3-bisbenzoyl-4,5-dimethyl- and 1,3-bisbenzoyl-2,4-dimethylbenzene | 60 |
| 7 | 1,2,4,5-tetramethyl | benzoyl 2.1 mol | $Fe_2O_3$ 5 mmol | 140 | 180 | 2 | 1,4-bisbenzoyl-2,3,5,6-tetramethylbenzene | 80 |
| 8 | 1,3,5-triethyl- | benzoyl 1.0 mol | $Fe_2O_3$ 5 mmol | 100 | 170 | 3 | 1,3-bisbenzoyl-2,4,6-triethylbenzene | 39 |
| 9 | 1,2,3,5-tetramethyl | benzoyl 2 mol | $Fe_2O_3$ 10 mmol | 150 | 180 | 3 | 1,3-bisbenzoyl-2,4,5,6-tetramethylbenzene | 74 |
| 10 | 1,3,5-trimethyl- | chloroacetyl 2.3 mol | $Fe_2O_3$ 0.5 mmol | 80 | 100 | 4 | 1,3-bischloroacetyl-2,4,6-trimethylbenzene (m.p. 129–131° C.) | 70 |
| 11 | 1,2,4,5-tetramethyl 2 mol | chloroacetyl 2.5 mol | $Fe_2O_3$ 0.5 mmol | 100 | 100 | 4 | 1,4-bischloroacetyl-2,3,5,6-tetramethylbenzene (m.p. 196° C.) | 55 |
| 12 | 1,2,3,5-tetra- | chloroacetyl | $Fe_2O_3$ | 100 | 100 | 4 | 1,3-bischloroacetyl- | 60 |

TABLE-continued

| Example | Benzene IV | Carbonyl chloride III | Amount of catalyst | $T_1$ [°C.] | $T_2$ [°C.] | t [h] | Product I | Yield [%] |
|---|---|---|---|---|---|---|---|---|
|  | methyl | 2.5 mol | 0.5 mmol |  |  |  | 2,4,5,6-tetramethyl-benzene (m.p. 125–127° C.) |  |
| 13 | 1,3,5-trimethyl- | benzoyl | FeSO$_4$x 7H$_2$0 10 mmol | 100 | 150 | 4 | 1,3-bisbenzoyl-2,4,6-trimethylbenzene | 68 |
| 14 | 1,3,5-trimethyl- | benzoyl | ZnO 20 mmol | 100 | 150 | 4 | 1,3-bisbenzoyl-2,4,6-trimethylbenzene | 77 |
| 15 | 1,3,5-trimethyl- | benzoyl | ZnCl$_2$ 20 mmol | 100 | 150 | 4 | 1,3-bisbenzoyl-2,4,6-trimethylbenzene | 74 |
| 16 | 1,3,5-trimethyl- | benzoyl | MoO$_3$ 20 mmol | 100 | 150 | 4 | 1,3-bisbenzoyl-2,4,6-trimethylbenzene | 78 |
| 17 | 1,3,5-trimethyl- | benzoyl | SnCl$_4$ 20 mol | 100 | 150 | 4 | 1,3-bisbenzoyl-2,4,6-trimethylbenzene | 79 |

We claim:

1. A process for preparing polyacylated aromatic compounds of the formula I

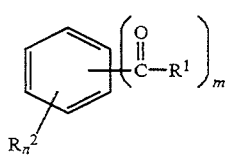

where
R$^1$ is phenyl which is unsubstituted or has inert substituents or is α-halo-C$_1$–C$_6$-alkyl, it being possible for these radicals to be identical or different;
R$^2$ is C$_1$–C$_4$-alkyl;
m is 2 or 3;
n is 0 to 4, it being possible for the R$^2$ substituents to be different when n>1,
with the proviso that m+n≦6, which comprises reacting an acylaromatic compound of the formula II

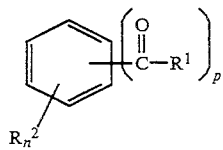

where p is 1 or 2, with a carbonyl halide of the formula III

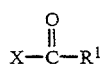

where X is halogen, in an amount appropriate for the desired degree of acylation, in the presence of catalytic amounts of Fe(II), Fe(III), Zn(II), Mo(VI), W(VI) or Sn(IV) compounds.

2. A process as defined in claim 1, wherein carbonyl chlorides Cl—CO—R$^1$ are used.

3. A process as defined in claim 1, wherein tri- or tetra-C$_1$–C$_4$-alkylacylbenzenes II are reacted.

4. A process as defined in claim 1, wherein the reaction is carried out in the presence of Fe$_2$O$_3$.

5. A process for preparing polyacylated aromatic compounds of the formula I

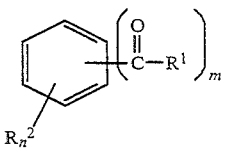

where
R$^1$ is phenyl which is unsubstituted or has inert substituents or is α-halo-C$_1$–C$_6$-alkyl, it being possible for these radicals to be identical or different;
R$^2$ is C$_1$–C$_4$-alkyl;
m is 2 or 3;
n is 0 to 4, it being possible for the R$^2$ substituents to be different when n>1,
with the proviso that m+n≦6, which comprises reacting an aromatic compound of the formula IV

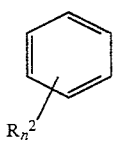

with a carbonyl halide of the formula III

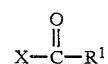

where X is halogen, in an amount appropriate for the desired degree of acylation, in the presence of catalytic amounts of Fe(II), Fe(III), Zn(II), Mo(VI), W(VI) or Sn(IV) compounds.

* * * * *